US00PP20688P3

(12) United States Plant Patent

Janse van Rensburg

(10) Patent No.: US PP20,688 P3

(45) Date of Patent: Jan. 26, 2010

(54) MANDARIN TREE NAMED 'VALLEY GOLD'

(50) Latin Name: *Citrus reticulata*
Varietal Denomination: Valley Gold

(75) Inventor: George Diederick Janse van Rensburg, Nelspruit (ZA)

(73) Assignee: Agricultural Research Council, Hatfield (ZA)

( * ) Notice: Subject to any disclaimer, the term of this patent is extended or adjusted under 35 U.S.C. 154(b) by 0 days.

(21) Appl. No.: 11/986,522

(22) Filed: Nov. 20, 2007

(65) Prior Publication Data

US 2009/0133172 P1 May 21, 2009

(51) Int. Cl.
*A01H 5/00* (2006.01)

(52) U.S. Cl. ..... Plt./202

(58) Field of Classification Search ..... Plt./201, Plt./202

See application file for complete search history.

(56) References Cited

U.S. PATENT DOCUMENTS

PP16,289 P3 * 2/2006 Roose et al. ..... Plt./202

OTHER PUBLICATIONS

UPOV-ROM GTITM, Plant Variety Database, 2008,/01, GTI Jouve Retrieval Software, Citation for plant 'Valley Gold'.*

"Certificate of grant of a Plant Breeder's Right," issued Nov. 7, 2004 in respect of plant *Citrus* L. (Mandarin), of variety Valley Gold. Department of Agriculture, Republic of South Africa. (1 page).

* cited by examiner

*Primary Examiner*—Susan B McCormick Ewoldt
(74) *Attorney, Agent, or Firm*—Morrison & Foerster LLP

(57) ABSTRACT

A new variety of mandarin (*Citrus L.*) designated 'Valley Gold' is described. The novel characteristics of the fruit include late onset of maturity of fruit, a distinct tougher rag and rind, and a darker external orange color (R.H.S. 28A) as compared to known varieties.

8 Drawing Sheets

Botanical/commercial classification: (*Citrus reticulata*), new hybrid mandarin variety.

Variety denomination: 'Valley Gold'.

BACKGROUND OF THE INVENTION

'Valley Gold' is a hybrid of *Citrus reticulata* variety Ellendale (not patented) (the seed parent) and an unpatented mandarin hybrid variety Robin (not patented) (the pollen parent). In 1980, pollen from 'Robin' was applied by hand to the stigmas of 'Ellendale'. The resulting fruits were collected in June 1981 whereafter seeds from each fruit were extracted and irradiated and thereafter planted in 1982. The resulting 73 seedlings were transplanted to a breeding orchard situated in Addo, in the Eastern Cape province of the Republic of South Africa (global positioning satellite co-ordinates 25°42'E; 33°34'S). These seedlings were not grafted and were grown on their own roots. Due to the so-called juvenility phenomenon in citrus trees as is known in the art, trees resulting from these transplanted seedlings only bore fruit in 1992. These trees were then evaluated for fruit quality traits. Based on the results of this evaluation, six of the aforementioned trees were selected for further evaluation, of which one of these selections resulted in the present 'Valley Gold' variety. Valley Gold was made subject of a South African Plant Breeders' Rights application in January 2000. This application was subsequently granted in 2004 under number ZA 20043214.

Fruit quality, and the time of fruit maturity (mid to end July), makes this selection a good candidate for the European market.

Severe to mild fruit splitting may occur in March or April, depending on rind thickness. However, crop load is still acceptable after split fruit has been dropped. Additionally, trees tend to be alternate-bearing.

'Valley Gold' was first asexually propagated in Addo, South Africa in 1995 when buds were collected from a hybrid seedling designated X83-2505/5, and then budded onto 'Carizzo citrange' rootstocks. Ten trees of 'Valley Gold' were planted in the field in September 1996 for description purposes. All characteristics of the original tree and its fruit as determined and described appear to be transmitted through succeeding asexual propagations. While 'Valley Gold' has been propagated and grown on 'Carizzo citrange' rootstock, no incompatibility or other rootstock related problems have been observed. The mother tree is growing on its own roots and is currently (2008) 24 years old. Although the tree condition is beginning to decline, the fruit quality is and always has been good.

Further, 'Valley Gold' has been cleansed of all viruses and viroids by shoot-tip grafting (STG), followed by pre-immunization with *Citrus tristeza* virus LMS6. This was done through a regulated process, which involves taking vegetative buds from the mother tree and introducing same into the South African Citrus Improvement Scheme. In this process, plant material is shoot-tip grafted to provide a virus-free source of bud wood material. Material so obtained is then pre-immunized with a mild strain of the aforementioned *Citrus tristeza* virus, followed by a certification by the Citrus Foundation Block.

The applicant is aware of U.S. Plant Pat. No. 16,289 ('289). The present variety is distinguishable over '289 in that, inter alia, not only is the present variety diploid whereas '289 is triploid, but also the respective rind colors differ.

BRIEF SUMMARY OF THE INVENTION

In this specification, all major color code designations are made with reference to the R.H.S. Colour Chart (1986) as provided by The Royal Horticultural Society of Great Britain.

This invention relates to a new and distinct variety of mandarin (*Citrus reticulata*), presently named 'Valley Gold' the novel characteristics of which, under the local South African evaluation conditions, reside particularly in the late onset of maturity of the fruit, as well as in a tougher rag and rind, and a darker orange external color of the rind, (Royal Horticultural Society of Great Britain RHS 28A).

BRIEF DESCRIPTION OF THE DRAWINGS

FIG. 2(*b*): is a photograph of the fruit showing the obloid shape and the dark orange (RHS 28A) rind color;

FIG. 4(*b*): is a photograph of the stem when viewed from a second perspective;

DETAILED BOTANICAL DESCRIPTION

Figure 1:
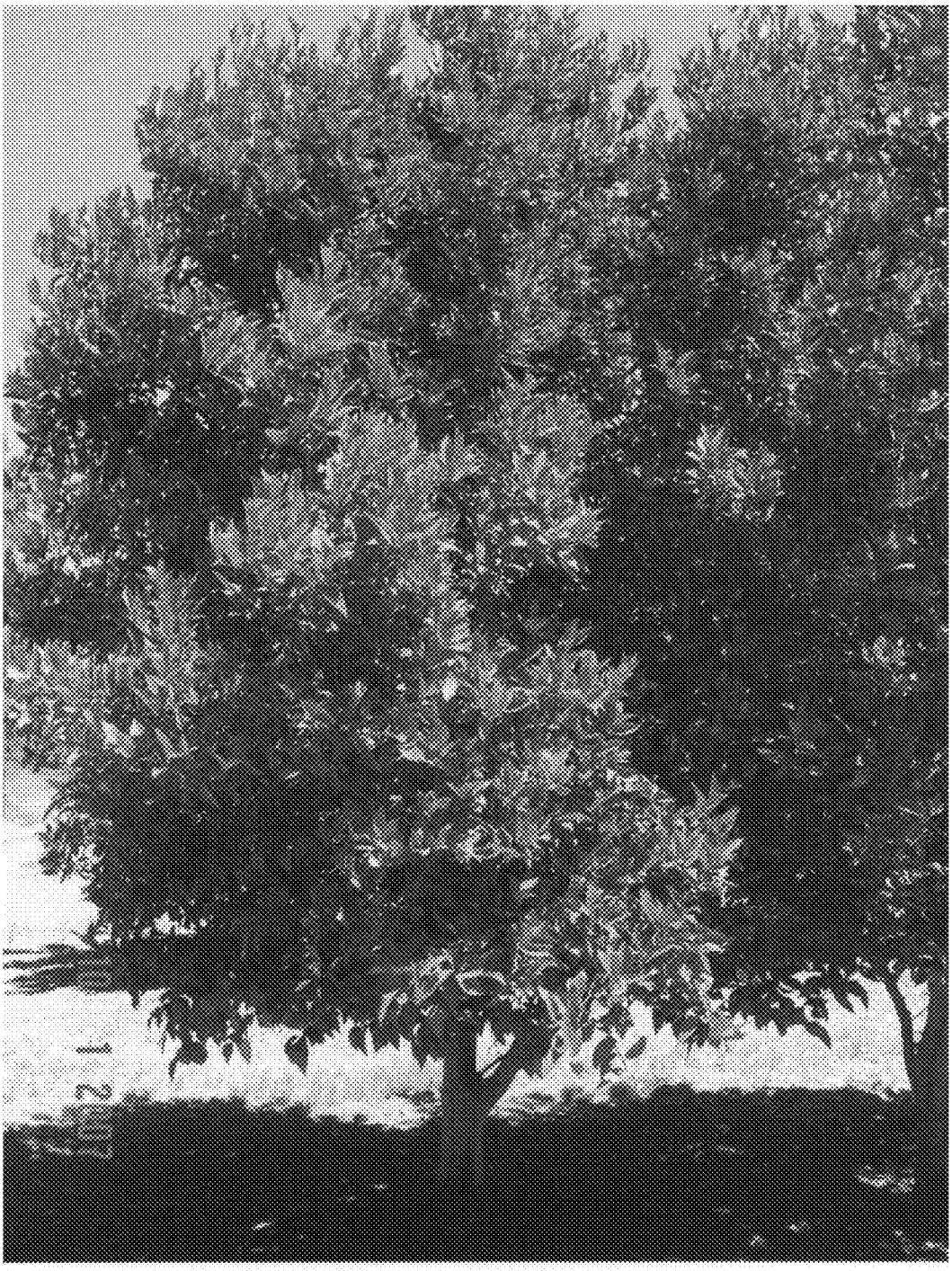
FIG. 1: is a photograph showing an entire tree.
Figure 2A:
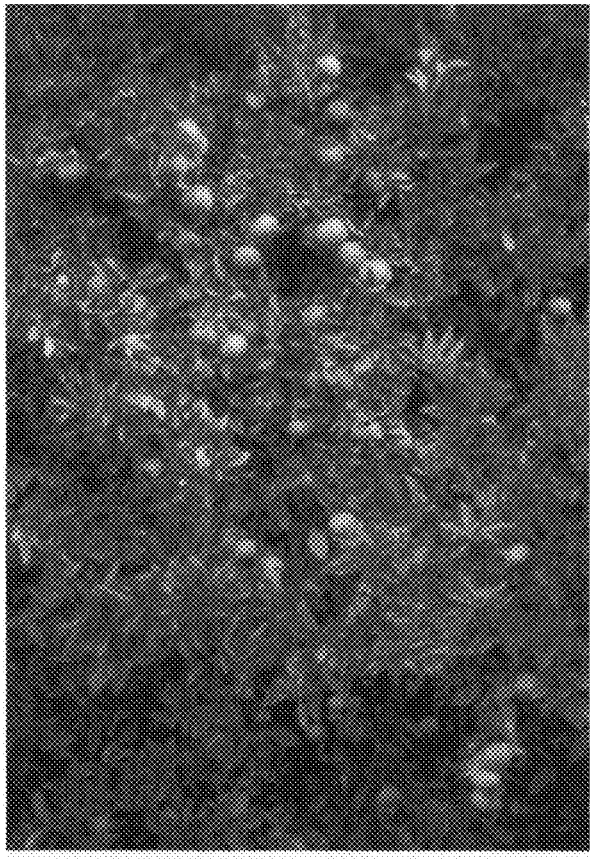
FIG. 2(*a*): is a photograph showing the crop load potential of 'Valley Gold' after fruit split has been dropped.
Figure 2B:
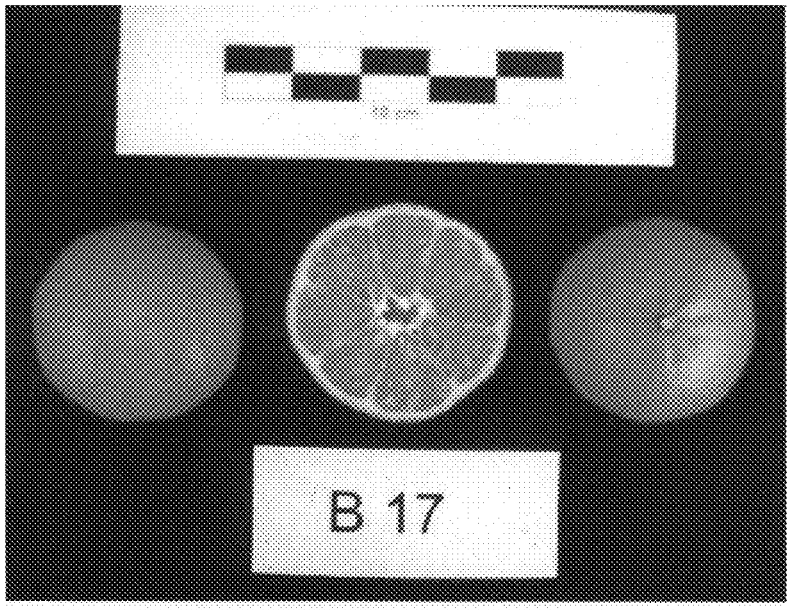
Figure 3:
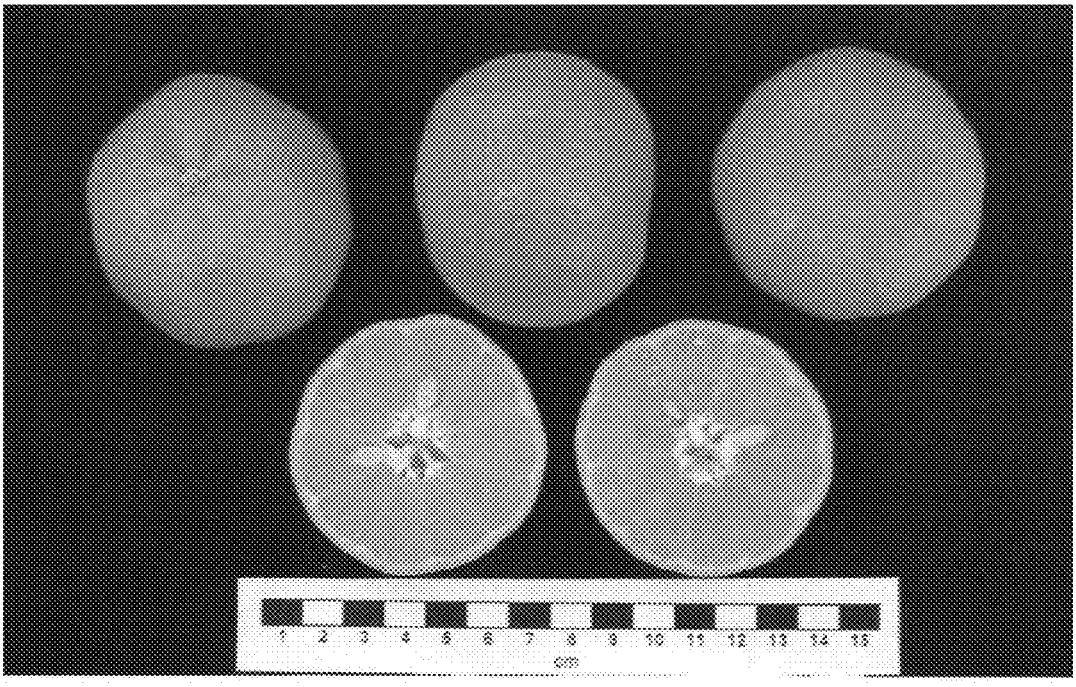
FIG. 3: is a further photograph showing details of 'Valley Gold' fruit: viewed from the side, apex, base and including a cross section through a fruit, illustrating the color (RHS 28A) of the rind.
Figure 4A:
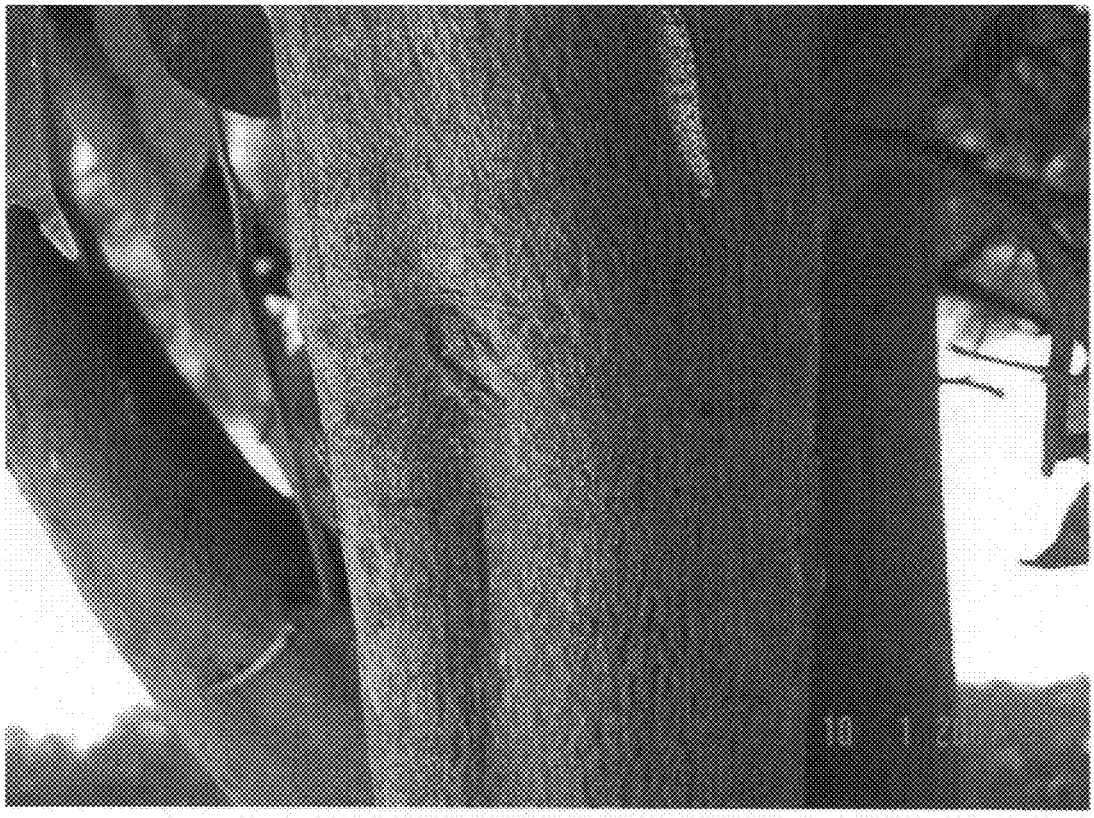
FIG. 4(*a*): is a photograph of the stem when viewed from a first perspective.
Figure 4B:
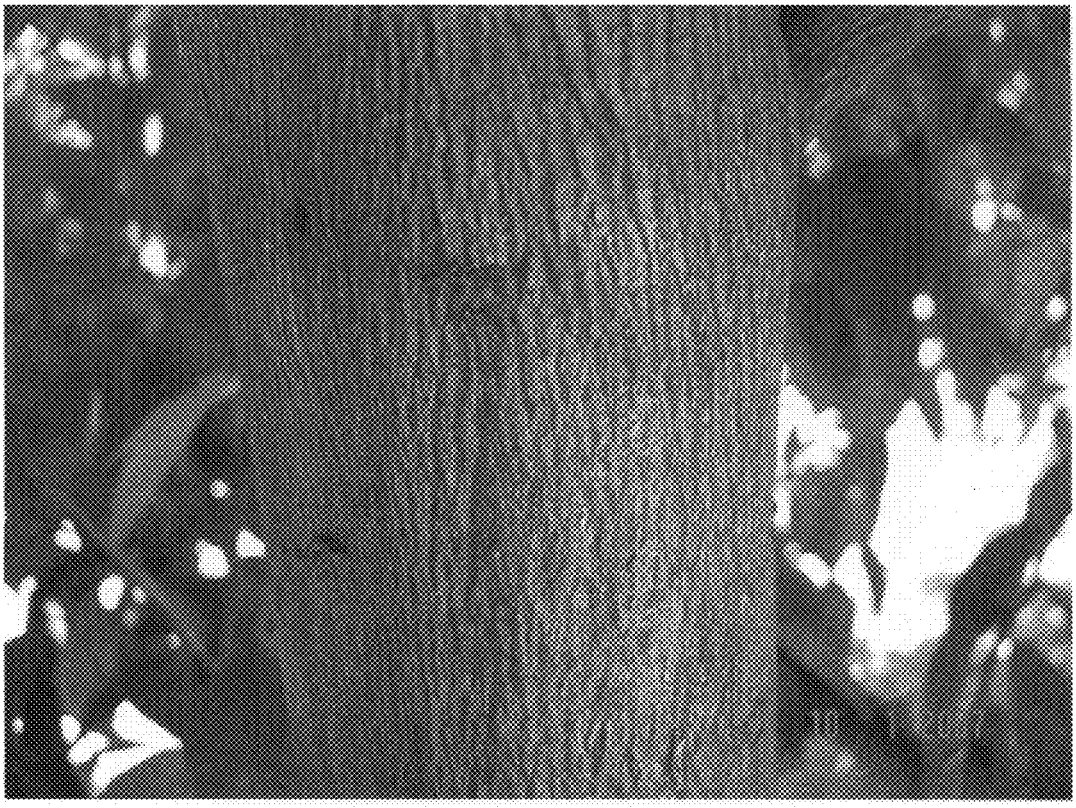
Figure 5:
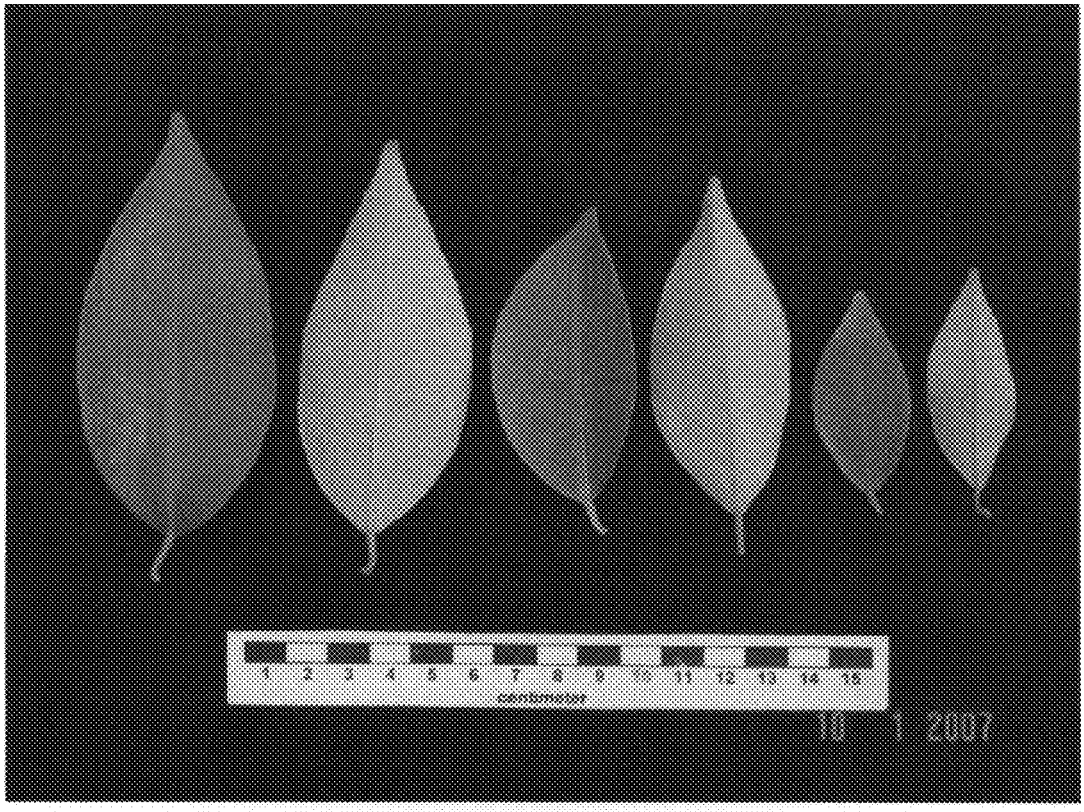
FIG. 5: is a close-up photograph showing several leaves of 'Valley Gold', illustrating the sizes and shapes of the leaves, including the venation thereof.
Figure 6:
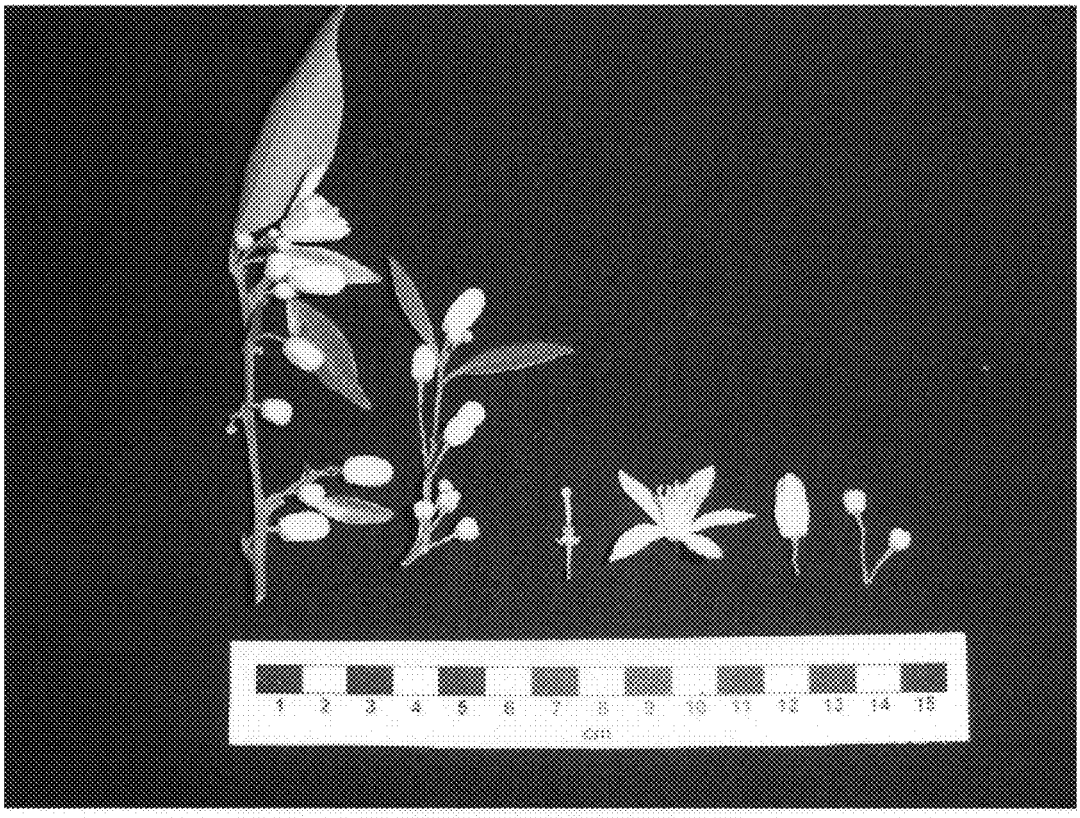
FIG. 6: is a photograph showing florescence.
Figure 7:
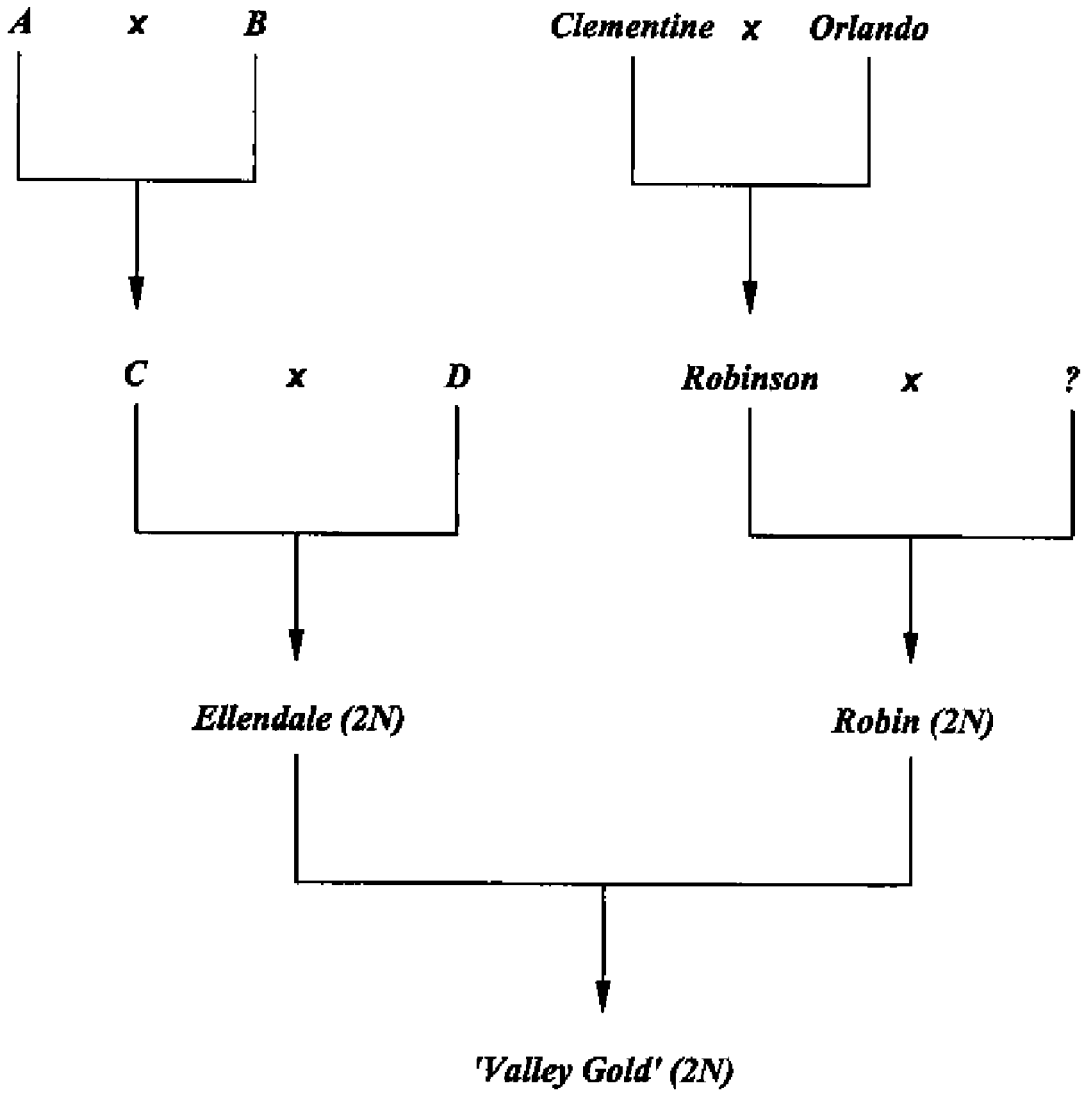
FIG. 7: is a schematic illustration of the pedigree of 'Valley Gold'.

The below detailed description is based on 4 to 6, and 11 year old trees, unless otherwise specifically stated to the contrary.

Tree: 'Valley Gold' trees are moderately spreading with small thorns, although fruit-bearing branches tend to become thornless. Tree vigor and density is medium. The rootstock compatibility with 'Carizzo citrange' is medium as observed and indicated by stem measurements. Also of significance is the fact that the 'Valley Gold' mother tree has thorns on its main branches, whereas the daughter trees are totally without thorns. The young trees in the nursery do not have any thorns and this is probably due to the fact that bud wood taken for propagation was from fruit-bearing branches, where the thorny juvenility has been outgrown.

*Shape.*—Ellipsoid; rectangular in shape.

*Size.*—The average height of trees is 4 meters, measured from soil level. The average spread (width) of trees is 3.3 meters.

*Trunk.*—The trunk has a smooth surface texture and is greyed-green (R.H.S. 197A) in color. The average trunk diameter is 453 millimeters measured at the bud union. Average diameters of 366 millimeters and 485 millimeters were measured at heights of 150 millimeters above and below the bud union, respectively. The average height of the bud union is 200 millimeters, measured above soil level.

*Branch.*—On average, branches have a circumference of 130 millimeters. There are also, on average, three main branches per tree, each having an average crotch angle of 55°. As with the trunk, the branches have a smooth surface texture and are greyish-brown (RHS 197A) in color.

Flower:

*Size and color.*—The flower of 'Valley Gold' is typically hermaphroditic. Its petals are yellow-white (RHS 158B) on the inside and yellow-white (R.H.S. 158B) with small yellow speckles (RHS 8C) on the outside. Further, it has light yellow (RHS 8C) anthers. Flowering occurs from September to October in South Africa. Being a normal diploid mandarin, pollen is abundant and has 66% viability, depending on climatic conditions, and as determined using the carmine-red stain method. Flower buds are ovoid in shape and have an average length of 11.6 millimeters and an average width of 5.8 millimeters. In addition, each flower has five petals. Petals are elliptic in shape and have an average length and width of 13.6 millimeter and 6 millimeter, respectively. The petal tip is acute in shape, while the base is truncate. The petal margin is entire. On a completely opened flower, the typical calyx diameter averages 5.2 millimeters. There are three flowers per cluster and the flowers have a typical citrus flower fragrance.

*Reproductive organs.*—The style has a length of 7.8 millimeters, while the stigma and the style, in combination, are approximately 9 millimeters long. The stamen has a length of 10.6 millimeters. On average, there is one style and stigma, and 18 stamens with anthers. The style is slightly longer than the stamen, with the result that the stigma is more prominent. It has been observed, albeit on a few rare instances, where the stamens and the styles are equal in length with the result that the stigma and the anthers are at the same height.

Leaves: For purposes of the following leaf description, all leaves were taken as the first leaf after the new flush growth.

*Shape and size.*—Leaves are simple, brevipetiolate and elliptic in shape, with slightly dentate incisions along the blade margin. Blade emargination is present at the tip. The leaves also have typically pinnate venation. The shape of the leaf apex is acuminate, while the base is typically rounded. In cross-section, the blade shape is straight or weakly concave. The length of a typical leaf blade is approximately 82 millimeters in length and the leaf blade also has a width of 34 to 44.7 millimeters. The ratio of length:width of the typical leaf is 2.41:1. The above dimensions were compared to 'Clem Late' (not patented) in a particular season for comparative purposes. 'Clem Late's' leaf blade length was 110 millimeters and the leaf blade was 43 millimeters wide. A further distinguishing feature of 'Valley Gold' with regard to 'Clem Late' is that the stalk attachment of 'Valley Gold' is larger than that of 'Clem Late'.

*Petiole.*—Wings are present but not prominent and are linear and narrow. Width of the wings is 1.5–2 millimeters. Length of the petiole is approximately 8 millimeters. In comparison, the petiole of 'Clem Late' is 10.9 millimeters.

*Color and surface texture.*—The adaxial (leaf upper) surface is darker (R.H.S. Green 137A to 137B), in comparison to the abaxial (leaf lower) surface (R.H.S. Yellow-green 146A. The leaf upper surface is smooth, while Leaf veins are prominent on the leaf lower surface, which also has a gritty texture due to the presence of little spots.

Fruit, external characteristics:

*Color.*—The rind color is dark orange and is fairly blemish-resistant (R.H.S. 28A).

*Rind.*—Fruit is easy to peel and the rind has an average thickness of 2 millimeters.

*Oil glands.*—Small oil glands are present, slightly pebbled and protruding and are uniform in size.

*Surface.*—Pubescence is absent on the fruit surface, and the fruit surface is slightly pebbled in appearance.

*Shape.*—With reference to the Citrus descriptors of the previously named International Plant Genetic Resources Institute (IPGRI), now known as Biodiversity International, the shape of 'Valley Gold' is obloid, having its broadest part in the middle of the fruit. The general shape of the proximal part of the fruit is slightly rounded, and has a neck. The length of the neck varies between 2 and 4 millimeters in length and is 12 millimeters thick.

*Size.*—Fruit is on average 47.1 millimeters in length and 60 millimeters in diameter. Individual fruit have on average a mass of 131.4 grams per fruit (see Table 1 below) on 'Carrizo citrange' rootstock. The fruit length:diameter ratio is 0.785.

*Base.*—Slightly rounded.

*Calyx.*—Slightly rounded.

*Apex.*—Slightly rounded.

*Areola.*—Present and smooth.

*Stylar scar.*—Present, but small in size.

Fruit, internal characteristics:

*Color.*—The internal flesh color is dark orange (R.H.S. 28A).

*Navel.*—Absent or rare when fruit is viewed internally.

*Glandular layer.*—Thickness of the rag is thin to normal, and slightly tough.

*Mesocarp (albedo).*—The adherence of the albedo to the pulp is weak and thus the peel is reasonably easy to remove from the pulp. Very few albedo strands are left behind after such removal. The albedo color is yellow-orange (R.H.S. 23D and 19C).

*Axis.*—Fruit has an open core, and a diameter of 14 millimeters. Further, the core has sparse to no filling.

*Segments.*—Each fruit has between eight to ten segments, and on average there are 9.6 well-developed segments per fruit.

*Pulp.*—Fine with large cells. In a transverse section of the fruit, the shape of the fruit pulp is scalloped.

*Juice.*—Fruit is juicy with good flavor. Acidity may only decline to acceptable levels by mid-July and may mask the flavor in high-acid areas. Fruit have an average juice percentage of 58.1% and 54.4%, on its own roots and on 'Carizzo citrange' rootstock, respectively. As indicated by the solids:acid ratio (see Table 1), the best time to harvest fruit under South African conditions is mid- to end-July.

*Seeds.*—Seeds are ovoid to semi-deltoid in shape with a mostly wrinkled surface. In this regard, approximately 20% of the seed surface tends to be smooth. Further, individual seeds have an average length of 0.94 millimeters and an average width of 0.6 millimeters. Furthermore, the seeds have a grey-white (RHS 155C/D) external color. Seed number is not excessive in mixed blocks and fruit are commercially seedless (no fruit has greater than 3 seeds) when caged. In a highly cross-pollinated scenario, 86.3% (see Table 1) of the fruit have between 1 and 3 individual seeds per fruit. Therefore, this selection should be almost seedless in a solid block although it is probably not self-incompatible.

TABLE 1

'Valley Gold' Mandarin Selections: Averages of Internal Quality Tests-2001 to 2006 Addo, Eastern Cape, South Africa

| Cultivers | Root-stock | Juice % | Brix % | Acid % | Brix:Acid Ratio | Rind Color |
|---|---|---|---|---|---|---|
| 'Valley Gold' | 'Carrizo' | 54.4 | 13.5 | 1.2 | 11.6 | 28 A |
| 'Valley Gold' | Own roots | 58.1 | 13.1 | 1.2 | 10.7 | 28 A |

| Cultives | Internal Color | Percentage fruit with 0 | 1-3 seed per fruit | 4-6 | 7+ | Avg. Fruit Mass (grams) |
|---|---|---|---|---|---|---|
| 'Valley Gold' | 28 A | 20.2 | 65.7 | 14.0 | 0.0 | 131.4 |
| 'Valley Gold' | 28 A | 1.2 | 86.3 | 12.5 | 0.0 | 107.3 |

TABLE 2

Internal Quality Tests (trees planted in 1984):

| Test Date | Juice % | Brix % | T. Acid % | Brix/TA Ratio |
|---|---|---|---|---|
| 28/06/1994 | 63 | 12.8 | 1.15 | 11.1 |
| 11/07/1997 | 58 | 11.2 | 0.98 | 11.4 |
| 14/08/2002 | 56 | 14.4 | 1.18 | 12.2 |
| 14/07/2004 | 60 | 13.0 | 1.14 | 11.4 |

*Yield.*—The average fruit yields across the time period 2001–2007 appear in Table 3 below:

TABLE 3

Average Fruit Yield (2001-2007)

| Year | 2001 | 2002 | 2003 | 2004 | 2005 | 2006 | 2007 |
|---|---|---|---|---|---|---|---|
| Tree age (years) | 4 | 5 | 6 | 7 | 8 | 9 | 10 |
| Yield (kg fruit/tree) | 12 | 26 | 45 | 51 | 63 | 53 | 55 |
| Yield (ton/ha) | 11 | 24 | 41 | 46 | 57 | 48 | 50 |

The fruit of 'Valley Gold' is intended for human consumption. Fruit stored and shipped at 4° C., and kept under these conditions, are likely to keep for up to 9 weeks (or 63 days).

The above-described new variety of Mandarin displays a distinct late expression of maturity (mid-end July), as well as a distinct tougher rag and rind, and a darker external orange color (R.H.S. 28A) as compared to known varieties.

What we claim is:

1. A novel and distinct variety of mandarin tree having the characteristics described and illustrated herein.

* * * * *